United States Patent [19]
Wang et al.

[11] Patent Number: 6,013,531
[45] Date of Patent: Jan. 11, 2000

[54] METHOD TO USE FLUORESCENT MAGNETIC POLYMER PARTICLES AS MARKERS IN AN IMMUNOASSAY

[75] Inventors: Chaeo-Huej J. Wang, Gurnee; Dinesh O. Shah, Vernon Hills, both of Ill.

[73] Assignee: Dade International Inc., Deerfield, Ill.

[21] Appl. No.: 08/518,135

[22] Filed: Aug. 22, 1995

Related U.S. Application Data

[63] Continuation of application No. 08/153,839, Nov. 17, 1993, abandoned, which is a continuation of application No. 07/451,274, Dec. 14, 1989, abandoned, which is a continuation-in-part of application No. 07/337,513, May 30, 1989, abandoned, which is a division of application No. 07/113,294, Oct. 26, 1987, abandoned.

[51] Int. Cl.⁷ .................. G01N 33/553; G01N 33/546
[52] U.S. Cl. .................. 436/526; 435/967; 436/518; 436/524; 436/525; 436/531; 436/533
[58] Field of Search .................. 435/962; 436/518, 436/524, 525, 526, 528, 531, 534, 800, 823, 824

[56] References Cited

U.S. PATENT DOCUMENTS

| | | | |
|---|---|---|---|
| 3,560,378 | 2/1971 | Weiss et al. | 210/680 |
| 3,700,555 | 10/1972 | Widmark et al. | 435/2 |
| 3,709,791 | 1/1973 | Lichtenstein | 52/107 |
| 3,843,450 | 10/1974 | Saxholm | 435/34 |
| 3,933,997 | 1/1976 | Hersh et al. | 436/526 |

(List continued on next page.)

FOREIGN PATENT DOCUMENTS

| | | |
|---|---|---|
| 0125995 | 11/1984 | European Pat. Off. . |
| 0149565 | 7/1985 | European Pat. Off. . |
| 0162819 | 11/1985 | European Pat. Off. . |
| 0169434 | 1/1986 | European Pat. Off. . |
| 0170446 | 2/1986 | European Pat. Off. . |
| 0177813 | 4/1986 | European Pat. Off. . |
| 0234083 | 9/1987 | European Pat. Off. . |
| 1501845 | 10/1973 | United Kingdom . |
| 2014162A | 8/1979 | United Kingdom . |
| 2017125 | 10/1979 | United Kingdom . |
| 2152664A | 8/1985 | United Kingdom . |
| 2161170A | 1/1986 | United Kingdom . |
| 8303920 | 11/1983 | WIPO . |
| WO 8300016 | 5/1984 | WIPO . |
| WO 8605815 | 10/1986 | WIPO . |
| WO8702063 | 4/1987 | WIPO . |
| WO 8303426 | 10/1987 | WIPO . |
| WO8904373 | 5/1989 | WIPO . |

OTHER PUBLICATIONS

Fornusek et al. CRC Critical Reviews in Therapeutic Drug Carrier Systems vol. 2 #2 (1986) 137–174.

"Elimination of B–lymphoma Cells from Human Bone Marrow: Model Experiments Usi Monodisperse Particles Coated with Primary Monoclonal Antibodies". 47 Cancer Res. 846 (Feb. 1, 1987) Kvalheim et al.

(List continued on next page.)

*Primary Examiner*—Lora M. Green
*Attorney, Agent, or Firm*—Cynthia G. Tymeson

[57] ABSTRACT

This invention provides a novel process of using magnetically responsive fluorescent polymer particles comprising polymeric core particles coated evenly with a layer of polymer containing magnetically responsive metal oxide as highly sensitive quantitative reagents for biochemical and immunological studies, wherein the fluorescent magnetic particles can serve as a marker for the number of particles. A wide variety of polymeric particles with sizes ranging from 1 to 100 microns can be used a core particles and transformed into magnetically responsive polymer particles. The surface of these magnetically responsive polymer particles can be coated further with another layer of functionalized polymer. These magnetically responsive fluorescent polymer particles can be used for passive or covalent coupling of biological material such as antigens, antibodies, enzymes or DNA/RNA hybridization and used as solid phase for various types of immunoassays, DNA/RNA hybridization probes assays, affinity purification, cell separation and other medical, diagnostic, and industrial applications.

4 Claims, 2 Drawing Sheets

U.S. PATENT DOCUMENTS

| | | |
|---|---|---|
| 3,985,649 | 10/1976 | Eddleman .............................. 210/695 |
| 4,018,691 | 4/1977 | Neal .................... 252/62.54 |
| 4,018,886 | 4/1977 | Giaver ..................... 436/526 |
| 4,021,308 | 5/1977 | Saxholm ............................ 435/288.3 |
| 4,070,246 | 1/1978 | Kennedy et al. ....................... 428/378 |
| 4,115,535 | 9/1978 | Giaver ..................... 436/526 |
| 4,157,323 | 6/1979 | Yen et al. ................ 522/84 |
| 4,169,804 | 10/1979 | Yape, Jr. ............................ 252/62.53 |
| 4,177,253 | 12/1979 | Davies et al. ........................... 436/526 |
| 4,206,094 | 6/1980 | Yen et al. ..................... 523/205 |
| 4,213,825 | 7/1980 | Saxholm ............................ 435/287.1 |
| 4,219,335 | 8/1980 | Ebersole ................................ 436/518 |
| 4,219,411 | 8/1980 | Yen et al. .............................. 209/213 |
| 4,230,685 | 10/1980 | Senyei et al. .......................... 436/526 |
| 4,241,176 | 12/1980 | Avrameas et al. ..................... 435/792 |
| 4,267,235 | 5/1981 | Rembaum et al. ..................... 428/407 |
| 4,272,510 | 6/1981 | Smith et al. ........................... 427/598 |
| 4,285,819 | 8/1981 | Yen et al. .............................. 210/679 |
| 4,292,920 | 10/1981 | Smith et al. ........................... 118/425 |
| 4,297,337 | 10/1981 | Mansfield et al. ..................... 436/537 |
| 4,331,654 | 5/1982 | Morris .................................... 424/450 |
| 4,335,094 | 6/1982 | Mosbach ................................ 424/137 |
| 4,339,337 | 7/1982 | Tricot et al. ......................... 252/62.54 |
| 4,342,739 | 8/1982 | Kakimi et al. .......................... 424/1.37 |
| 4,369,226 | 1/1983 | Rembaum .............................. 428/334 |
| 4,371,624 | 2/1983 | Saxholm ............................ 435/287.7 |
| 4,382,982 | 5/1983 | Whilans .................................. 427/130 |
| 4,385,126 | 5/1983 | Chen et al. ............................. 436/518 |
| 4,416,813 | 11/1983 | Ikeda et al. ............................ 530/354 |
| 4,438,068 | 3/1984 | Forrest ...................................... 422/61 |
| 4,438,179 | 3/1984 | Solc ..................................... 4287/407 |
| 4,438,239 | 3/1984 | Rembaum et al. .................... 525/54.1 |
| 4,452,773 | 6/1984 | Molday .................................. 424/1.37 |
| 4,490,436 | 12/1984 | Kawakami et al. ..................... 428/403 |
| 4,496,658 | 1/1985 | Kondo et al. .......................... 435/7.94 |
| 4,508,625 | 4/1985 | Graham .................................. 210/695 |
| 4,546,035 | 10/1985 | Ko et al. .............................. 428/315.9 |
| 4,552,812 | 11/1985 | Marget et al. .......................... 428/407 |
| 4,554,088 | 11/1985 | Whitehead et al. .................. 252/62.54 |
| 4,563,419 | 1/1986 | Ranki et al. ................................. 435/6 |
| 4,563,510 | 1/1986 | Ugelstad et al. .......................... 526/66 |
| 4,576,912 | 3/1986 | Yaverbaum et al. ..................... 435/7.1 |
| 4,582,622 | 4/1986 | Ikeda et al. ........................... 252/62.54 |
| 4,601,753 | 7/1986 | Soileau et al. ........................... 428/404 |
| 4,612,247 | 9/1986 | Walsh et al. ............................. 428/402 |
| 4,624,923 | 11/1986 | Margel .................................... 424/1.37 |
| 4,626,371 | 12/1986 | Ikenaga et al ........................ 252/62.54 |
| 4,628,037 | 12/1986 | Chagnon et al. ........................ 436/526 |
| 4,638,032 | 1/1987 | Benner ................................. 525/54.11 |
| 4,672,040 | 6/1987 | Josephson .............................. 436/526 |
| 4,707,523 | 11/1987 | Chang et al. ............................ 525/372 |
| 4,783,336 | 11/1988 | Margel et al. ........................... 424/462 |
| 4,891,324 | 1/1990 | Pease et al. .............................. 436/519 |
| 4,935,147 | 6/1990 | Ullman et al. ........................... 210/695 |
| 4,948,739 | 8/1990 | Charmot .................................. 436/533 |
| 4,985,233 | 1/1991 | Klaveness et al. ................... 424/9.323 |

OTHER PUBLICATIONS

"T Cell Repertoire: Receptors, Subsets, Cell Functions—Isolation of Pure an Functionally Active T4 and T8 Cells by Positive Selection with Antibody Coate Monosized Magnetic Microspheres", XIX Transplantation Proceedings 265 (Feb. 1, 1987) Leivestad et al.

Vartdal et al., "HLA Class I and II Typing Using Cells Positively Selected fr Blood by Immunomagnetic Isolation—A fast and Reliable Technique", Tissue Antigens 300 (1986).

Reynolds et al., "Model System for Removing Neuroblastoma Cells from Bone Marro Using Monoclonal Antibodies and Magnetic Immunobeads", 46 Cancer Res. 5882 (1986).

Seger et al. "Removal of Neuroblastoma Cells from Bone Marrow with Monoclonal Antibodies and Magnetic Immunobeads, Transfusion Medicine: Recent Technological Advances", p. 285 (1986).

Kemshead et al. "Magnetic Microspheres and Monoclonal Antibodies for the Depletion of Neuroblastoma Cells from Bone Marrow: Experiences, Improvements, and Observations", 54 Br. J. Cancer (1986).

Leivestad et al. "Isolation of Functionally Active T–Cell by Monoclonal Antibodies Conjugated to Monodisperse Magnetic Microspheres (M–450)", XVIII Transplantation Proceedings No. 4, 731 (1986).

Leivestad et al. "Positive Selection of Activated T Cells of the T8 (CD8) Sub–type by Immunomagnetic Separation", 28 Tissue Antigens 46 (1986).

Lea et al. "Characterization of Human Mononuclear Cells After Positive Selection with Immunomagnetic Particles", 23 Scand. J. Immunol., 509 (1986).

Gaudernack et al. "Isolation of Pure Functionally Active CD8 T Cells", 90 J. of Imm. Meth. 179 (1986).

Seeger et al. "Depletion of Neuroblastoma Cells from Bone Marrow with Monoclonal Antibodies and Magnetic Immunobeads", Advances in Neuroblastoma Research 443 (1985).

Lea et al. "Magnetic Monosized Polymer Particles for Fast and Specific Fractionation of Human Mononuclear Cells", 22 Scand. J. Immol. 207 (1985).

Kemshead et al. "Removal of Malignant Cells from Bone Marrow Using Magnetic Microspheres and Monoclonal Antibodies", 29 Prog. Exp. Tumor Res. 249 (1985).

Treleaven et al. "Removal of Neuroblastoma Cells from Bone Marrow with Monoclonal Antibodies Conjugated to Magnetic Microspheres", The Lancet (Jan. 14, 1984).

Margel et al. "Novel Effective Immunoadsorbents Based on Agarose–Polyaldehyde Microsphere Beads: Synthesis and Affinity Chromatography", 128 Anal. Biochem. 342 (1982).

Vartdal et al. "Depletion of T Lymphocytes from Human Bone Marrow", 43 Transplantation 366 (1978).

Margel et al. "A Novel Synthesis of Polyacrolein Microspheres and Their Application for Cell Labeling and Separation". Immunol–Comm.1981; 10(7):567–75.

Pourfarzaneh et al. "The Use of Magnetizable Particles in Solid Phase Immunoassay", 28 Method Biochem. Anal. 267 (1982).

The Lancet, Jan. 14, 1984. Removal of Neuroblastoma Cells from Bone Marrow . . . J.G. Treleaven et al.

Elsevier 1984 "Microspheres and Drug Therapy". S.S. Davis et al.

METHOD TO USE FLUORESCENT MAGNETIC POLYMER PARTICLES AS MARKERS IN AN IMMUNOASSAY

This is a continuation of U.S. Ser. No. 08/153,839, filed Nov. 17, 1993, now abandoned, which is a continuation of U.S. Ser. No. 07/451,274, filed on Dec. 14, 1989, now abandoned, which in turn is a continuation-in-part of U.S. Ser. No. 07/337,513, filed May 30, 1989, now abandoned, which in turn is a divisional of U.S. Ser. No. 07/113,294, filed Oct. 26, 1987, now abandoned.

FIELD OF THE INVENTION

This invention relates to a method to use magnetically responsive fluorescent polymer particles as highly sensible fluorescent markers in biochemical and immunological studies.

BACKGROUND OF THE INVENTION

Many biological techniques, such as immunoassays, affinity purification etc., require the separation of bound from free fractions. Magnetic particles have been used to facilitate the desired separation.

Magnetic particles have been formed from a variety of particulate and magnetic matter, using a variety of processes, having different characteristics. For example, Ikeda et al. U.S. Pat. No. 4,582,622, discloses a magnetic particle comprised of gelatin, water-soluble polysaccharide, sodium phosphate and ferromagnetic substances; U.S. Pat. Nos. 4,628,037 and 4,554,088 disclose magnetic particles comprised of a magnetic metal oxide core surrounded by a coat of polymeric silane; U.S. Pat. No. 4,452,773 discloses discrete colloidal sized particles having a core of ferromagnetic iron oxide ($Fe_3O_4$) which is coated with a water-soluble polysaccharide or a derivative thereof having functional groups; and Mansfield U.S. Pat. No. 4,297,337 discloses magnetic glass- or crystal-containing material as a particulate carrier.

SUMMARY OF THE INVENTION

The present invention provides a novel process of using magnetically responsive fluorescent polymer particles, as highly sensitive quantitative reagents for biochemical and immunological studies. The fluorescent magnetic particles can serve as a marker for a correct number of particles being delivered to an assay well and for detecting particle loss during the assay.

These fluorescent magnetic particles with or without coupling to biological material can be incorporated at various ratios to nonmagnetic particles for various assays to serve as markers for making sure that the correct number of particles are being delivered into the well and for checking the particle loss during the assay.

The fluorescent magnetic particles of this invention may be prepared by first producing a magnetically responsive metal oxide, hereinafter referred to as metal oxide, with average size of about 1 micron or less and then coating a fluorescent polymeric core particle with a layer of polymer containing metal oxide. The surface of these fluorescent magnetic particles can be coated further with another layer of polymer or functionalized polymer to provide the desired surface characteristics.

The spectral characteristics of these fluorescent magnetic particles can be varied by using core particles incorporated with various fluorescent dyes, either a single fluorescent dye or a combination of several fluorescent dyes. Alternatively, the fluorescent magnetic particles of the present invention can be prepared by incorporating various fluorescent dyes, either a single fluorescent dye or a combination of several fluorescent dyes, which are soluble in the monomer and can withstand the polymerization condition, in the presence of nonfluorescent polymeric core particles, metal oxide, and monomer.

The fluorescent magnetic particles produced by the present invention are monodispersed in size with rough surface and have a magnetic metal oxide content of from about 5% to 50%, preferably from 10% to 25%. The fluorescence intensity of these fluorescent magnetic particles can be adjusted by varying the magnetic metal oxide content to vary the shading due to the metal oxide and/or varying the amount of fluorescent dye incorporated into the fluorescent polymeric core particles.

Particles with these characteristics have been found to be useful in immunoassays and a wide variety of biomedical applications. These fluorescent magnetic particles can be used for passive or covalent coupling of biological material such as antigens, antibodies, enzymes or DNA/RNA and used as solid phase for various types of immunoassays, DNA/RNA hybridization assays, affinity purification, cell separation, phagocytosis, and other biomedical applications.

OBJECTIVES AND ADVANTAGES

It is the objective of this invention to:

Develop a process of producing magnetically responsive fluorescent polymer particles easily from readily available polymer particles.

Develop a process of producing magnetically responsive fluorescent polymer particles with moderate sedimentation and fast magnetic separation.

Develop a process of producing magnetically responsive fluorescent polymer particles with various surface charges, and functional groups for passive adsorption or covalent coupling of biological material.

Develop medical, biological, diagnostic and industrial applications using these magnetically responsive fluorescent polymer particles.

Develop a means to monitor an assay using fluorescent magnetic particles.

The advantages of this invention include:

A wide variety of fluorescent polymeric core particles with size from about 1 to 100 microns can easily be transformed to magnetically responsive particles.

The metal oxide content can be varied according to the applications.

The surface can be derivatized into a wide variety of functional groups for covalent coupling.

A wide variety of monomer can be used for the final coating to provide different surface characteristics of the resulting polymer.

Both crosslinked and noncrosslinked magnetically responsive fluorescent polymer particles can be produced.

Monodispersed magnetically responsive fluorescent polymer particles can be produced.

DETAILED DESCRIPTION OF THE INVENTION

The fluorescent magnetic particles of this invention may be prepared by first producing metal oxide with average size of about 1 micron or less. The metal oxide is produced by heating and precipitating a mixture of divalent and trivalent metal salt, preferably a mixture of ferrous and ferric sulfate or chloride with sodium hydroxide solution. The molar ratio of divalent to trivalent metal salt can be varied from 0.5 to 2.0, preferably 0.5 to 1.0 to obtain the desirable size and magnetic characteristics of metal oxide. It is observed that the molar ratio of divalent to trivalent metal salt affects the size of the metal oxide: the smaller the molar ratio of divalent to trivalent metal salt, the smaller the size of metal oxide. The molar ratio of divalent to trivalent metal salt also affects the color of the resulting magnetic particles: the smaller the molar ratio, the lighter the brownish color of the resulting magnetic particles. Preferably, the metal oxide is either superparamagnetic or paramagnetic although ferromagnetic metal oxide can also be used, provided centrifugation instead of magnetic separation is used during the clean up.

Other divalent transition metal salts such as manganese, magnesium, cobalt, nickel, zinc, and copper salts may be substituted for ferrous salt.

After the metal oxide has been precipitated, it is washed several times with centrifugation at 250×g until the supernatant is neutral in pH. The metal oxide is resuspended in deionized water and mechanically stirred at high speed to break down the aggregate of metal oxide crystals. Further centrifugation at 250×g will not pellet all of the metal oxide. The supernatant which contain smaller size metal oxide crystals is collected and the pellet is resuspended in deionized water. This process is repeated for at least three times or until most of metal oxide can no longer be pelleted at 250×g. The metal oxide obtained this way usually has size less than 2.0 micron. Low speed centrifugation at 100×g to remove larger crystals will reduce the size to less than 0.8 micron.

The metal oxide with average size of 1.0 micron or less is mixed with monomer and coated onto the fluorescent polymeric core particles, preferably polystyrene particles, with size of 1 to 100 microns in the presence of initiator. Addition of a small quantity of emulsifier will help prevent the particles from agglomerating. The fluorescent magnetic particles are then coated with a protective layer of polymer, preferably polystyrene, to prevent the metal oxide from falling off. If functionalized fluorescent magnetic particles are desired, the magnetic particles can be coated further with another layer of functionalized polymer to provide functional groups such as carboxyl, amino or hydroxyl for covalent coupling of biological material.

Figure 1:
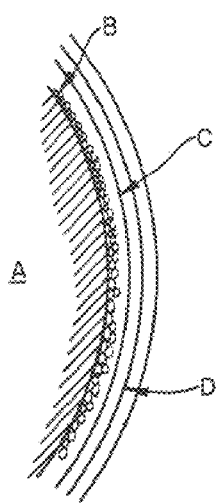
FIG. 1 represents a fluoresent magnetic particle prepared according to this invention.
Figure 2:
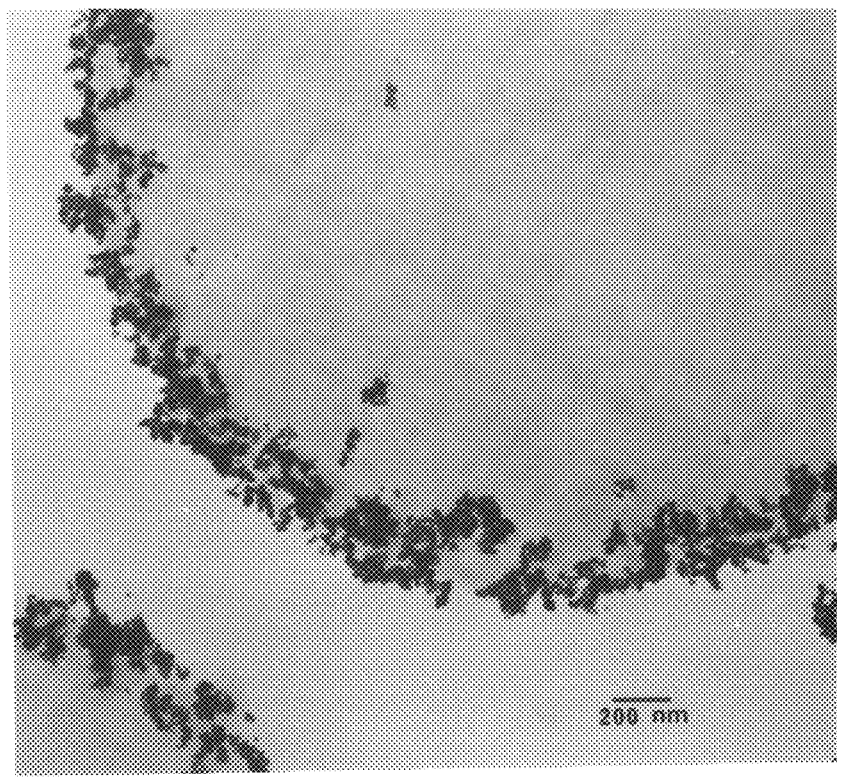
FIG. 2 shows the transmission electron micrograph of a 0.08 to 0.1 micron slice of magnetic particle prepared according to this invention.
Figure 3A:
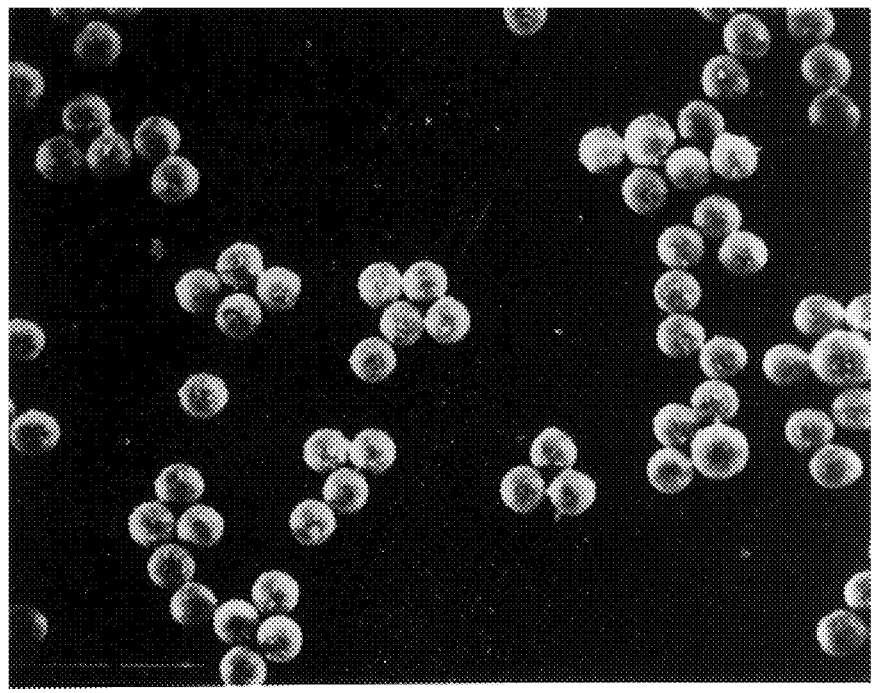
FIGS. 3a and 3b show a scanning electron micrograph of 6.8 micron meagnetic particles prepared according to this invention.
Figure 3B:
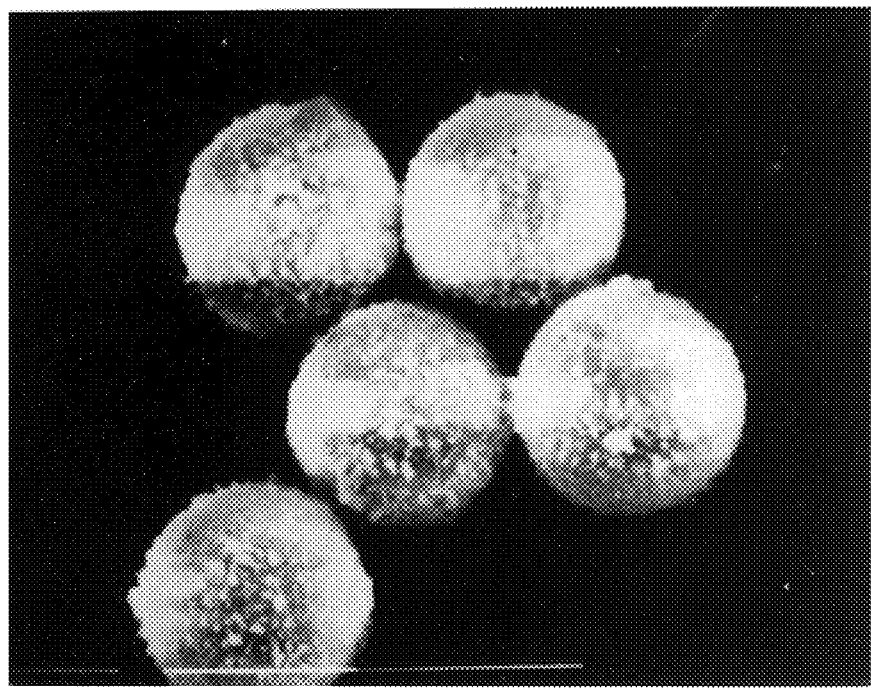

The fluorescent magnetic particles prepared according to this invention can be illustrated in FIG. 1, where 1 represents the fluorescent core particle, 2 represents the metal oxide/polymer coating, 3 represents the protective polymer coating and 4 represents the functionalized polymer coating. FIG. 2 shows the transmission electron micrograph of 0.08 to 0.1 micron slice of a magnetic particle prepared according to this invention. FIGS. 3a and 3b show a scanning electron micrograph of 6.8 micron magnetic particles, prepared according to this invention. FIG. 3a is at 1000× and FIG. 3b is at 5000× magnification.

The fluorescent polymeric core particles useful in this invention may be of any polymer which can be obtained as a dispersion of small particles and which can absorb a monomer thereby causing the metal oxide and monomer mixture to coat onto the surface of the core particles. The core particles may be of any size and shape, preferably of 1 to 100 microns in size and spherical in shape. When monodispersed core particles are used the resulting magnetic particles will also be monodispersed in size. The core particles may be obtained by emulsion polymerization, suspension polymerization or other means of polymerization with or without a crosslinking agent such as divinyl benzene or the like. Among the monomers which can be used to prepare core particles are styrene, methyl methacrylate, vinyltoluene and the like. A mixture of the monomers can also be used. The fluorescent core particles may be obtained by incorporating the fluorescent dye to the core particles, using various techniques known to those skilled in the art. The monomer used for magnetic metal oxide coating or protective coating may or may not be the same type as the fluorescent core particles. The weight ratio of monomer used for metal oxide coating to fluorescent core particles may be from 0.1 to 12, preferably from 0.2 to 6, depending upon the thickness of metal oxide/polymer layer desired. When the metal oxide prepared from a mixture of ferrous and ferric salts is used for coating it is preferred to use a monomer to fluorescent core particle weight ratio of about 0.1 to 0.5. However when the metal oxide prepared from a mixture of manganese (II) and ferric salts is used for coating the weight ratio of monomer to core particles may be from 0.1 to 12. As a result when crosslinked fluorescent magnetic particles which are inert to common organic solvent are desired, it is preferred to use the metal oxide prepared from a mixture of manganese (II) and ferric salts with monomer containing 2% to 10%, preferably 8% to 10% by weight of crosslinking agent and a monomer to core particle weight ratio of 3 to 12, preferably 4 to 6 and a monomer to fluorescent dye weight ratio of 0.1 to 10. When lower monomer to core particle weight ratio (i.e. 0.1 to 0.5) is used during the metal oxide/polymer coating it is preferred to overcoat the resulting fluorescent magnetic particles with a protective layer of polymer coating to further adhere the metal oxide to the surface of the fluorescent magnetic particles. However, when higher monomer to core particle ratio (i.e. 3 to 12) is used no protective polymer coating is necessary. The polymerization temperature may be from 50° C. to 90° C., preferably 55° C. to 65° C. The polymerization initiator may either be water soluble such as potassium persulfate and the like or water insoluble such as benzoyl peroxide and the like. Other means of polymerization initiation such as radiation, ionization or the like may also be used. It is found unexpectedly that fluorescent magnetic particles can be produced without using any emulsifier when the metal oxide prepared from a mixture of manganese (II) and ferric salts is used for coating. However, a small amount of emulsifier such as sodium dodecylsulfate, Aerosol 22, Tween 20 or Nonidet P-40 (NP 40) is found to be useful in preventing the particles from extensive aggregation during the metal oxide/polymer coating when the metal oxide prepared from a mixture of ferrous and ferric salts is used for coating. Other emulsifiers with the same capability may also be used. The magnetic metal oxide content can be varied from 5% to 50%, preferably from 10% to 25% by using different amount of metal oxide during the metal oxide/polymer coating. Multiple metal oxide/polymer coatings can also be employed to increase the metal oxide content. Other ingredients commonly used in polymerization may also be added as long as magnetic particles with desirable characteristics can be obtained. The ingredients for metal oxide/polymer coating may be added all at once at the beginning of metal oxide/polymer coating process or added stepwise. When the metal oxide prepared from a mixture of ferrous and ferric salt is used, it is preferred to add the ingredients stepwise. The ingredients may be mixed by mechanic stirring, tumbling or other means of agitation under vacuum or inert gas such as argon. The functional groups can be incorporated onto the surface of the fluorescent magnetic particles by either using a mixture of monomer and functionalized monomer during the metal oxide/polymer coating or overcoating the magnetic particles with a thin layer of functionalized monomer at the end. The functionalized monomer used may be selected from one or a mixture of the following: 2-hyrdoxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein glutaraldehyde and the like. The magnetic fluorescent particles can also be overcoated with a layer of different polymer than the one used for metal oxide/polymer coating or protective coating to take up the surface characteristics of that polymer.

Applications of Fluoresent Magnetic Particles

The fluorescent material that can be incorporated includes X trap 33. The uses of a wide variety of fluorescent magnetic particles as solid phase for various applications such as fluorescence immunoassays, radioimmunoassays, enzyme immunoassays, cell separations, enzyme immobilizations and affinity purifications, have been reviewed in literature as examplified by the following articles: Hirschbein et al, Chemical Technology, March 1982, 172–179 (1982); Pourfarzaneh, The Ligand Quarterly, 5(1): 41–47 (1982); Halling and Dunnill, Enzyme Microbe Technology, 2: 2–10 (1980); Mosbach and Anderson, Nature, 270: 259–261 (1977); Guesdon et al, J. Allergy Clinical immunology, 61(1), 23–27 (1978). Some applications have also been disclosed in the U.S. Pat. Nos. 4,152,210 and 4,343,901 for enzyme immobilizations; U.S. Pat. Nos. 3,970,518, 4,230,685, and 4,267,2343 for cell separations; U.S. Pat. Nos. 4,554,088, 4,628,037, and 3,933,997 for immunoassays.

Some magnetic particles may be useful in one application, but not in another application. For example, the magnetic particles disclosed in U.S. Pat. Nos. 4,554,088 and 4,628,037, which comprise a superparamagnetic metal oxide core generally surrounded by a coat of polymeric silane, may be useful in immunoassay and affinity purification, due to the large surface area and slower settling rate, but are not suitable in cell separation application such as bone marrow purging. Due to the small size of the magnetic particles, disclosed in these two patents, it is very diffictilt to remove all of the magnetic particles from the cell suspension effectively. Moreover, the nonspecific binding of smaller magnetic particles to normal cells would be much higher. In using magnetic particles for bone marrow purging, the magnetic particles are coated with antibody, such as sheep anti-mouse IgG, and the bone marrow is treated with a mixture of several monoclonal antibodies against the cancer cell surface antigens. The magnetic particles will bind only to the cancer cells and cause them to be separated from normal cells by passing them through a strong magnetic field. The cleansed cells are then put back into the patient.

By using the processes of this invention magnetic particles can be optimized in terms of size, surface area, metal oxide content and surface characteristics for a wide variety of biomedical applications. The magnetic particles produced by this invention can be used as solid phase for enzyme immunoassay, fluorescence immunoassay, radioimmunoassay, DNA/RNA hybridization assay, and other diagnostic applications. Immunoassays can be performed by using various configurations such as sandwich assays and competitive binding assays etc., which are obvious to those skilled in the art. The DNA/RNA hybridization can also be performed by using various configurations such as solid phase hybridization or liquid phase hybridization. In solid phase hybridization configuration a DNA or RNA probe (catcher probe) is immobilized on the magnetic particle first. The immobilized catcher probe is then used to hybridize with complimentary strand of DNA from the sample (sample DNA). Finally another probe (signal probe) which is labeled with fluorescent, radioactive or enzyme tracer and capable of hybridizing with another part of the sample DNA is used for signal generation. In liquid phase hybridization configuration the catcher probe and signal probe are allowed to hybridize with the sample DNA in the liquid phase first and then immobilized to the magnetic particles.

Alternatively, the signal probe can also be labelled with one or several biotin groups and the signal is detected by binding the biotin groups with avidin labelled fluorescent, radioactive or enzymatic tracer to enhance the sensitivity of the assay.

The immunoassays and DNA/RNA hybridization assays can be used to measure a wide variety of compounds such as drugs, hormones, antibodies, peptides, DNA, RNA, nucleotides, viral antigens, and carbohydrates in biological samples.

The magnetic particles produced by this invention can also be used for affinity purification, cell separation, enzyme immobilization and other biomedical applications. In cell separation the magnetic particles are used to either remove unwanted cells (negative selection) or enrich the wanted cells (positive selection) through immunological reactions or nonimmunological reactions. This principle can be used to remove cancer cells from bone marrow (bone marrow purging), purify cell populations through either positive or negative selection for tissue culture and perform various cellular immunoassays etc. In affinity purification the magnetic particles are used in place of conventional solid phase such as polyacrylamide gels, sepharose gels or other cellulose beads to purify a wide variety of biological materials such as antibodies, antigens, enzymes, inhibitors, cofactors, single stranded DNA, binding proteins, haptens and carbohydrates etc. In another application similar to the affinity purification, the magnetic particles can be used to cross adsorb and remove unwanted protein components from the antisera or clinical samples. In enzyme immobilization the enzyme is immobilize onto the magnetic particles through various means of coupling so as to preserve the enzyme activity and to permit the reuse of immobilized enzyme. The magnetic particles with immobilized enzyme can be used to replace other solid phases such as glass beads, controlled pore glass, silica gels and cellulose beads etc., which are commonly used in immobilized enzyme systems to produce a wide variety of materials such as carbohydrates, amino acids, and proteins, etc.

These fluorescent magnetic particles with or without coupling to biological material can be incorporated at various ratios to nonmagnetic particles for various assays as mentioned in Examples 42 and 43 to serve as markers for making sure that the correct number of particles are being delivered into the well and for checking the particle loss during the assay.

These applications are all facilitated by the ease of separation, fast reaction rate and large surface area common to most of magnetic particles. The following examples are provided to further illustrate the versatility and advantages of this invention, the details thereof are not to be construed as limitations, for it will be apparent that various equivalents, changes and modifications may be resorted to without departing from the spirit and scope thereof and it is understood that such equivalent embodiments are intended to be included therein.

General Procedure for the Preparation of Metal Oxide

EXAMPLE 1

In a three-necked round bottom flask equipped with mechanical stirrer, condenser, thermometer, dropping funnel and heating mantle was placed a mixture containing 0.361 mol of ferrous sulfate and 0.369 mol of ferric sulfate ($Fe^{++}/Fe^{+++}$ ratio=1) in 400 ml of deionized water. The mixture was heated to 85 to 90° C. with stirring and added dropwise 850 ml of 6 N sodium hydroxide over a period of 90 minutes. The mixture was stirred at 85 to 90° C. for one more hour and cooled to room temperature. The metal oxide precipitates were centrifuged at 250×g for 10 minutes. The clear supernatant was decanted and the pellet was resuspended in 900 ml of deionized water using mechanical stirrer. This cleaning process was repeated six times or until the supernatant was almost neutral in pH. The supernatant was decanted and resuspended in 200 ml of deionized water. Further centrifugation at 250×g will not pellet all of the metal oxide precipitates. The supernatant which contained smaller size metal oxide crystals was collected and the pellet was resuspended in 200 ml of deionized water. This process was repeated for at least three times or until most of metal oxide can no longer be pelleted at 250×g. The metal oxide obtained this way usually has size less than 2.0 micron. The combined metal oxide suspension was centrifuged at 100×g for 10 minutes. The supernatant was collected to give 800 ml of 8.6% w/v magnetic metal oxide suspension having the size less than 0.8 microns.

EXAMPLE 2

Same procedures as described in Example 1 were followed except 0.235 mol of ferrous sulfate, 0.297 mol of ferric sulfate ($Fe^{++}/Fe^{+++}$ ratio=0.79) in 400 ml of deionized water and 480 ml of 6 N sodium hydroxide were used to give 2000 ml of 2.86% w/v suspension of magnetic metal oxide.

EXAMPLE 3

Same procedures as described in Example 1 were followed except 0.178 mol of ferrous sulfate, 0.298 mol of ferric sulfate ($Fe^{++}/Fe^{+++}$ ratio=0.59) in 400 ml of deionized water and 520 ml of 6 N sodium hydroxide were used to give 1500 ml of 2.98% w/v suspension of magnetic metal oxide.

EXAMPLE 4

Same procedures as described in Example 1 were followed except 0.15 mol of ferrous sulfate, 0.276 mol of ferric sulfate ($Fe^{++}/Fe^{+++}$ ratio=0.54) in 400 ml of deionized water and 520 ml of 6 N sodium hydroxide were used to give 700 ml of 6.88% w/v suspension of magnetic metal oxide.

EXAMPLE 5

Same procedures as described in Example 1 were followed except 0.116 mol of manganese sulfate and 0.146 mol of ferric sulfate ($Mn^{++}/Fe^{+++}$ ratio=0.79) in 225 ml of deionized water and 240 ml of 6 N sodium hydroxide were used to give 1700 ml of 1.8% w/v suspension of magnetic metal oxide.

Preparation of Magnetic Particles

EXAMPLE 6

A mixture containing 600 ml of deionized water, 6 ml of styrene and 80 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 850 ml of 5% w/v, 4.0 micron polystrene particles. The bottle was resealed, evacuated and rotated for one hour and added 50 ml of 2% sodium dodecylsulfate. After five more hours 6 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 1.6 l with deionized water to give a 2.5% w/v suspension with about 11% magnetic metal oxide content and 4.3 micron average size.

EXAMPLE 7

The magnetic particles, 1.6 l of 2.5% w/v, prepared as described in Example 6, were carboxylated by adding 1 g of sodium dodecylsulfate, 10 g of potassium persulfate and a solution containing 0.98 ml of undecylenic acid and 0.02 ml of divinyl banzene in 4 ml of methanol. The mixture was placed in a sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 680 ml with deionized water to give a 5.8% w/v suspension with about 11% magnetic metal oxide content and 4.3 micron average size.

EXAMPLE 8

A mixture containing 600 ml of deionized water, 6 ml of styrene and 80 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 850 ml of 4.78% w/v, 6.1 micron polystrene particles. The bottle was resealed, evacuated, rotated for five hours and added 6 ml of styrene and 10 g of potassium persulfate. The mixture was rotated for another fifteen hours, filtered through two layers of cheese cloth, separated magnetically and washed several times with deionized water until the supernatant was clear. The resulting magnetic particles were resuspended to 1.5 l with deionized water and carboxylated by adding 1 g of sodium dodecylsulfate, 10 g of potassium persulfate and a solution containing 0.98 ml of undecylenic acid and 0.02 ml of divinyl benzene in 4 ml of methanol. The mixture was placed in a sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 800 ml with deionized water to give a 4.3% suspension with about 11.6% magnetic metal oxide content and 6.8 micron average size.

EXAMPLE 9

A mixture containing 600 ml of deionized water, 6 ml of styrene and 60 ml of 8.6% w/v magnetic metal oxide prepared as described in Example 1, was placed in a three-necked round bottom flask and stirred at 67° C. for one hour under argon. To the mixture were added 12 g of potassium persulfate and 470 ml of 5% w/v, 2.7 micron polystrene particles. The mixture was stirred at 67° C. for one hour and added 30 ml of 2% sodium dodecylsulfate. After stirring at 67° C. under argon for five more hours 6 ml of styrene and 6 g of potassium persulfate were added to the mixture. The mixture was stirred at 67° C. under argon for another fifteen hours, filtered through two layers of cheese cloth, separated magnetically and washed several times with deionized water until the supernatant was clear. The resulting magnetic particles were resuspended to 900 ml with deionized water and carboxylated by adding 0.6 g of sodium dodecylsulfate, 10 g of potassium persulfate and a solution containing 0.598 ml of undecylenic acid and 0.012 ml of divinyl benzene in 2.4 ml of methanol. The mixture was placed in sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 500 ml to give a 6.5% w/v suspension with about 14% magnetic metal oxide content and 4.0 micron average size.

EXAMPLE 10

A mixture containing 600 ml of deionized water, 6 ml of styrene and 60 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 470 ml of 5% w/v, 2.7 micron polystyrene particles. The bottle was resealed, evacuated and rotated for one hour and added 30 ml of 2% sodium dodecylsulfate. After five more hours 6 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 500 ml with deionized water to give a 6.8% w/v suspension with about 14% magnetic metal oxide content and 4.0 micron average size.

EXAMPLE 11

A mixture containing 180 ml of deionized water, 2 ml of styrene and 20 ml of 8.6% w/v magnetic metal oxide, prepared as described in Example 1, was placed in a sealed bottle. The bottle was evacuated and rotated at about 60 rpm in a 55° C. oven for one hour. To the mixture were added 4 g of potassium persulfate and 160 ml of 6.8% w/v magnetic particles (3.0 micron, 14% metal oxide content), prepared as described in Example 10. The bottle was resealed, evacuated and rotated for one hour and added 10 ml of 2% sodium dodecylsulfate. After 5 more hours 2 ml of styrene and 2 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 160 ml with deionized water to give a 7.78% w/v suspension with about 19% metal oxide content and 4.2 micron average size.

EXAMPLE 12

A mixture containing 90 ml of deionized water, 1 ml of styrene and 10 ml of 8.6% w/v magnetic metal oxide, prepared as described in Example 1, was placed in a sealed bottle. The bottle was evacuated and rotated at about 60 rpm in a 55° C. oven for one hour. To the mixture were added 1 g of potassium persulfate and 80 ml of 7.78% w/v magnetic particles (3.2 micron, 19% metal oxide content), prepared as described in Example 11. The bottle was resealed, evacuated and rotated for four hour and added 5 ml of 2% sodium dodecylsulfate. After 5 more hours 1 ml of styrene and 1 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 160 ml with deionized water to give a 4.5% w/v suspension with about 23% metal oxide content and 4.5 micron average size.

EXAMPLE 13

A mixture containing 400 ml of deionized water, 1.92 ml of styrene, 0.08 ml of divinyl benzene, 4 g of potassium persulfate, 20 g of 200–400 mesh 4% divinyl benzene cross linked polystyrene beads and 10 ml of 8.6% w/v magnetic metal oxide, prepared as described in Example 1, was placed in a sealed bottle. The bottle was evacuated and rotated at about 60 rpm In a 55° C. oven for 15 hours. The mixture was allowed to settle and the supernatant was decanted. The resulting magnetic beads were resuspended in 200 ml of deionized water and allowed to settle again. This process was repeated several times until the supernatant was clear. The resulting magnetic beads were resuspended in 200 ml of deionized water and added 0.1 g of sodium dodecyl sulfate. 2.0 g of potassium persulfate, 0.48 ml of styrene, and 0.02 ml of divinyl benzene. The bottle was resealed, evacuated and rotated at about 60 rpm in a 55° C. over for one hour and added a solution containing 0.098 ml of undecylenic acid and 0.002 ml of divinyl benzene in 0.4 ml of methanol. The mixture was rotated for four more hours and cleaned up by gravitational sedimentation as described previously. The water was removed by filtration and the carboxyl magnetic beads were dried to give 20 g of 200–400 mesh carboxyl magnetic beads.

EXAMPLE 14

A mixture containing 100 ml of deionized water, 0.5 ml of styrene, 2 g of potassium persulfate, 75 ml of 5% w/v 4.0 micron polystrene particles and 10 ml of 6.88% w/v magnetic metal oxide. prepared as described in Example 4, was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting magnetic particles were resuspended to 150 ml with deionized to give a 2.5% w/v suspension with about 14% metal oxide content and 4.3 micron average size.

EXAMPLE 15

Same procedures as described in Example 14 were followed except 20 ml of 6.88% w/v magnetic metal oxide, prepared as described in Example 4, was used to give 160 ml of 2.5% w/v suspension with about 18% metal oxide content and 4.3 micron average size.

EXAMPLE 16

A mixture containing 2000 ml of deionized water, 13 ml of styrene and 550 ml of 2.98% w/v magnetic metal oxide prepared as described in Example 3, was placed in a sealed bottle. The bottle was evacuated and rotated at about 60 rpm in a 55° C. oven for one hour. To the mixture were added 20 g of potassium persulfate and 950 ml of 10% w/v, 3.0 micron polystyrene particles. The bottle was resealed, evacuated and rotated for one hour and added 60 ml of 2% sodium dodecylsulfate. After five more hours 8 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 3000 ml with deionized water to give a 3.38% w/v suspension with about 12% magnetic metal oxide content and 3.2 micron average size.

EXAMPLE 17

A mixture containing 150 ml of magnetic particles (3.2 micron, 3.38% w/v with 12% metal oxide content) prepared as described in Example 16, 2 ml of 1% NP 40, 0.5 ml of methyl methacrylate or styrene, 1 g of potassium persulfate and 2 ml of functionalized monomer, trimethylammoniumethyl methacrylate methosulfate (40% aqueous solution), was placed in a sealed bottle. The bottle was rotated at about 60 rpm in a 55° C. oven for four hours. The mixture was filtered through two layers of cheese cloth, separated magnetically and washed several times with deionized water until the supernatant was clear. The resulting magnetic particles were resuspended to 200 ml with deionized water to give a 2.5% w/v suspension of magnetic particles with trimethylammonium functional groups on the surface.

EXAMPLE 18

Same procedures as described in Example 17 were followed except 1 ml of functionalized monomer, 2-aminoethyl methacrylate, was used to give 200 ml of 2.5% w/v suspension of magnetic particles with amino groups on the surface.

EXAMPLE 19

Same procedures as described in Example 17 were followed except 1 ml of functionalized monomer, 2-hydroxyethyl methacrylate was used to give 200 ml of 2.5% w/v suspension of magnetic particles with hydroxyl groups on the surface.

EXAMPLE 20

Same procedures as described in Example 17 were followed except 1 ml of monomer, 1-vinyl-2-pyrrolidinone, was used to give 200 ml of 2.5% w/v suspension of magnetic particles with polyvinylpyrrolidinone on the surface.

EXAMPLE 21

Same procedures as described in Example 17 were followed except 1 g of functionalized monomer, methyl propene sulfonic acid, was used to give 200 ml of 2.5% w/v suspension of magnetic particles with sulfonic acids groups on the surface.

EXAMPLE 22

Same procedures as described in Example 17 were followed except 1 ml of functionalized monomer, dimethylaminoethyl methacrylate, was used to give 200 ml of 2.5% w/v suspension of magnetic particles with dimethylamino groups on the surface.

EXAMPLE 23

A mixture containing 20 ml of 7.0% w/v, 2.11 micron polystyrene particles, 100 ml of 1.8% w/v metal oxide prepared as described in Example 5, 50 ml of deionized water and a solution containing 0.15 g of benzoyl peroxide in 7.5 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting magnetic particles were resuspended to 200 ml with deionized water to give 5.0% w/v suspension with about 16.8% metal oxide content and 3.6 micron average size.

EXAMPLE 24

A mixture containing 20 ml of 7.0% w/v, 2.11 micron polystyrene particles, 100 ml of 1.8% w/v metal oxide prepared as described in Example 5, 50 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 5.0% w/v suspension with about 16.8% metal oxide content and 3.6 micron average size. The crosslinked magnetic particles prepared this way were found to be uniform in size and inert to common organic solvents such as acetone, acetonitrile and dimethyl formamide.

EXAMPLE 25

A mixture containing 20 ml of 7.0% w/v, 2.11 micron polystyrene particles, 150 ml of 1.8% w/v metal oxide prepared as described in Example 5 and a solution containing 0.15 g of benzoyl peroxide, 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 5.4% w/v suspension with about 23% metal oxide content and 4.0 micron average size. The crosslinked magnetic particles prepared this way were found to be uniform in size and inert to common organic solvents such as acetone, actonitrile and dimethyl formamide.

EXAMPLE 26

A mixture containing 15 ml of 9.16% w/v, 3.2 micron polystyrene particles, 100 ml of 1.8% w/v metal oxide prepared as described in Example 5, 55 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 4.7% w/v suspension with about 16.8% metal oxide content and 5.5 micron average size. The crosslinked magnetic particles prepared this way were found to be uniform in size and inert to common organic solvents such as acetone, actonitrile and dimethyl formamide.

EXAMPLE 27

A mixture containing 30 ml of 4.5% w/v, 4.1 micron polystyrene particles, 100 ml of 1.8% w/v metal oxide prepared as described in Example 5, 40 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 4.5% w/v suspension with about 16.9% metal oxide content and 6.7 micron average size. The crosslinked magnetic particles prepared this way were found to be uniform in size and inert to common organic solvents such as acetone, acetonitrile and dimethyl formamide.

EXAMPLE 28

A mixture containing 20 ml of 7.0% w/v, 2.11 micron polystyrene particles, 100 ml of 1.8% w/v metal oxide prepared as described in Example 5, 50 ml of deionized water and a solution containing 0.15 g of benzoyl peroxide, 0.75 ml of undecylenyl alcohol and 0.75 ml of divinyl benzene in 6 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked hydroxyl magnetic particles were filtered and dried to give 9 g of powder with about 16.8% metal oxide content and 3.9 micron average size. The crosslinked hydroxyl magnetic particles prepared this way were found to be uniform in size and inert to common organic solvents such as acetone, acetonitrile and dimethyl formamide.

Coupling Biological Material to Magnetic Particle

EXAMPLE 29

In a 80 ml bottle was place 30 ml of 4.3 micron, 5.0% w/v carboxyl magnetic particles prepared as described in Example 7. The particles were separated magnetically and resuspended in 50 ml of phosphate buffer (0.1 M, pH 5.5). To the particle suspension were added 20 mg of bovine serum albumin and 100 mg of 1-ethyl-3-(3-dimethylaminopropyl)-carbodiimide (EDC). The mixture was rotated end to end at room temperature for two hours and separated magnetically. The particles were washed once with 80 ml of phosphate buffer and resuspended to 75 ml with phosphate buffered saline (0.1 M, pH 7.0) to give a 2.0% w/v suspension.

To couple bovine serum albumin to magnetic particles by passive adsorption the same procedures were followed except no EDC was used.

EXAMPLE 30

In a 4 ml vial was placed 1 ml of 4.3 micron, 5.0% w/v carboxyl magnetic particles prepared as described in Example 7. The particles were separated magnetically and washed once with 2 ml of phosphate buffer (0.1 M, pH 5.5) and resuspended to 2 ml with the same buffer. To the particles suspension were added 140 ml of 1.4 mg/ml Goat (Gt) anti Mouse (Ms) IgG and 10 mg of 1-ethyl-3-(3-dimenthylaminopropyl) carbodiimide. The vial was rotated end to end at room temperature for two hours. The particles were separated magnetically, washed once with 2 ml of phosphate buffet and resuspended to 2 ml with phosphate buffered saline (0.1 M, pH 7.0) to give a 2.5% w/v Gt anti Ms IgG coated magnetic particles. Other kinds of antibody either monoclonal or polyclonal could also be coupled to carboxyl magnetic particles by using the same procedures.

To couple Gt anti Ms IgG or other kind of antibody to the magnetic particles by passive adsorption the same procedures were followed except no EDC was used.

EXAMPLE 31

In a 4 ml vial was placed a 2.5 ml of bovine serum albumin coated magnetic particles (4.3 micron, 2% w/v) prepared as described in Example 29. The particles were separated magnetically and resuspended to 2 ml with phosphate buffer (0.1 M, ph 5.5). To the mixture were added 10 ul of Ms anti B red cells surface antigen (20 mg/ml) and 1 mg of 1-ethyl-3-(3-dimethylaminopropyl)-carbodiimide. The mixture was rotated end to end at room temperature for two hours. The particles were separated magnetically, washed once with phosphate buffer and resuspended in 2 ml of phosphate buffered saline (0.1 M, pH 7.0) to give a 2.5% w/v suspension.

EXAMPLE 32

Same procedures as described in Example 31 were followed except using 40 ul of Ms anti A red cells surface antigen (5 mg/ml) to give 2 ml of 2.5% w/v suspension.

Blood Typing Using Magnetic Particles

EXAMPLE 33

In a 5 mm×65 mm test tube labeled A was placed 25 ul of 2.5% w/v Ms anti A coated magnetic particles prepared as described in Example 32. To the other test tube labeled B was placed 25 ul of 2.5% w/v Ms anti B coated magnetic particles prepared as described in Example 31. To both test tubes was added 50 ul of 1% packed red blood cells prepared by 1 to 100 dilution of packed red blood cells in isotonic buffered saline. The test tubes were shaked by finger tapping for several times and placed on the top of a magnet. The results were summarized as follows:

|  | BLOOD TYPE | | | |
| --- | --- | --- | --- | --- |
|  | A | B | O | AB |
| TUBE A | + | − | − | + |
| TUBE B | − | + | − | + |

Where + represent a positive reaction, meaning the red cells were agglutinated by the corresponding antibody coated magnetic particles as a result the supernatant in the test tube was clear after magnetic separation. On the other hand the supernatant of a negative reaction would remain cloudy after magnetic separation due to the absence of agglutination between the red cells and the antibody coated magnetic particles.

Immunoassays Using Magnetic Particles

EXAMPLE 34

In a 2 ml microcentrifuge tube was placed 1 ml of 6% w/v, 3 micron carboxyl magnetic particles. The particles were centrifuged for 3 minutes at 10000 rpm. The supernatant was aspirated and the particles were resuspended by vortexing with 1 ml of 5 to 100 ug/ml recombinant HBcAg in acetate buffer. The tube was rotated at room temperature for two hours and centrifuged as described before. The supernatant was aspirated and the particles were resuspended in 1 ml of overcoat solution containing acetate buffer and 2 to 10% of normal animal serum. The tube was rotated at room temperature for 2 to 16 hours and centrifuged as described before. The supernatant was aspirated and the particles were washed three times with 1 ml of isotonic buffered slaine (IBS) by centrifugation and resuspension. Finally, the particles were resuspended with 1 ml of IBS and stored at 2 to 8° C.

EXAMPLE 35

To the first two columns of a 96-well microtiter plate was placed 20 ul of 0.25% w/v hepatitis B core antigen (HBcAg) coated magnetic particles prepared as described in Example 34. Sample preparation consisted of various dilutions of a HBcAb positive serum into a negative plasma, followed by a 1:100 dilution of each sample into specimen dilution buffer (SDB). The SDB contained phosphate buffer, protein stabilizers, detergent, and antimicrobial agents. To the wells containing the particles were added 50 ul of each final sample dilution. After 30 minutes incubation at 37° C., the particles were separated for two minutes on a magnetic separator and washed three times with 200 ul wash buffer containing salts and detergent. To each well containing the particles was added 50 ul of goat antihuman IgG-B-D-galactosidase conjugate (0.5 ug/ml) in diluent containing salts, protein stabilizers, glycerol, detergent and antimicrobial agents. After 15 minutes incubation at 37° C. the particles were separated and washed three times as described above and resuspended in 30 ul of IBS. The particles were transferred to the first two columns of a black microtiter plate (Dynatech). To each well containing the particles was added 100 ul of a solution containing 4-methylumbelliferyl-B-galactopyranoside (MUG, Sigma). The plate was incubated at 37° C. and the fluorescence intensity was measured by using a Fluorescence Concentration Analyzer (FCA, Pandex) equipped with 365 nm excitation and 450 nm emission filters at five minutes interval and 10×gain setting. The increase in fluorescence intensity in a five minutes interval was recorded in arbitrary fluorescence unit (AFU) and presented in Table I.

TABLE I

| Dilution of Positive Specimen | AFU (5 Minutes) Average of Two Wells |
| --- | --- |
| 1:100 | 22687 |
| 1:1000 | 5933 |
| 1:5000 | 1516 |
| 1:8000 | 835 |
| 1:10000 | 639 |
| 1:15000 | 495 |

TABLE I-continued

| Dilution of Positive Specimen | AFU (5 Minutes) Average of Two Wells |
| --- | --- |
| 1:20000 | 427 |
| 1:25000 | 307 |

EXAMPLE 36

The coupling of mouse antiHBsAg to carboxyl magnetic particles was similar to Example 30.

To the wells of a black 96-well microtiter plate (Dynatech) were added 20 ul of 0.25% w/v, 3.2 micron, mouse antiHBsAg coated carboxyl magnetic particles in duplicate. To the wells containing the magnetic particles was added 100 ul of neat plasma containing various amounts of HBsAg or a HBsAg-negative plasma. After 30 minutes incubation at 37° C., the particles were separated for two minutes on a magnetic separator and washed once with 100 ul of wash buffer containing salts and detergent. To each will containing the particles was added 20 ul of mouse antiHBsAg—B-galactosidase conjugate in diluent containing salts, protein stabilizers, glycerol, detergent and antimicrobial agents. After 15 minutes incubation at 37° C., the particles were separated and washed five times as described above. To each will containing the particles was added 50 ul of a solution containing 4-methylumbelliferyl-B-D-galactopyranoside (MUG, Sigma). The plate was incubated at 37° C. and the fluorescence intensity was measured by using a Fluorescence Concentration Analyzer (FCA, Pandex) equipped with 365 nm excitation and 450 nm emission filters or five minutes interval and 10×gain setting. The increase in fluorescence intensity in a five minutes interval was recorded in arbitrary fluorescence unit (AFU) and presented in Table II.

TABLE II

| HBsAg Conc. (nano gm) | AFU (5 Minutes) Average of Two Wells |
| --- | --- |
| 1.0 | 1149 |
| 0.5 | 455 |
| 0.25 | 218 |
| 0.125 | 118 |
| neg. | 14 |

EXAMPLE 37

The HIV-1 antigens from HTLV-IIIB/H-9 cells (Gallo Strain) were coupled to 3.6 micron carboxyl magnetic particles by using similar procedures as described in Example 34.

To the wells of a 96-well microtiter plate were added 20 ul of 0.25% w/v of HIV coated magnetic particles in duplicate. To the wells containing the particles were added 50 ul of positive, borderline and negative specimens diluted 1:100 in specimen dilition buffer (SDB) containing phosphate buffer, protein stabilizers, detergent and antimicrobial agents. After 30 minutes incubation at 37° C., the particles were separated for two minutes on a magnetic separator and washed three times with 100 ul of washed buffer containing salts and detergent. To each well containing particles was added 50 ul of goat antihuman-B-galactosidase (approximately 0.5 ug/ml) conjugate in diluent containing salts, protein stabilizers, glycerol, detergent and antimicrobial agents. After 15 minutes incubation at 37° C., the particles were washed four times as described above. The particles were transferred to the black microtiter plate (Dynatech). To each well containing particles was added 100 ul of a solution containing 4-methylumelliferyl-B-D-galactopyranoside (MUG, Sigma). The plate was incubated at 37° C. and the fluorescence intensity was measured by using a Fluorescence Concentration Analyzer (FCA, Pandex) equipped with 365 nm excitation and 450 nm emission filters at five minutes intervals and 25×gain setting. The increase in fluorescence intensity in a five minutes interval was recorded in arbitrary fluorescence unit (AFU) and presented in Table III.

TABLE III

| Anti-HIV Specimens | AFU (5 minutes) Average of Two Wells |
| --- | --- |
| Positive Control | 9462 |
| Borderline Specimen | 527 |
| Negative Control | 86 |

Cell Separation Using Magnetic Particles

EXAMPLE 38

The 4.3 micron carboxyl magnetic particles prepared as described in Example 7 were washed and sonicated in phosphate buffered saline (PBS, pH 7.7), sterilized in 70% ethanol for 10 minutes, washed three times in PBS and incubated for 48 hours at 4° C. with affinity-purified sheep anti-mouse immunoglobulin antibody (SAM) at 0.5 mg/ml and a ratio of 3.3 mg antibody/100 mg particles. Before use, the antibody coated magnetic particles were washed in PBS and resuspend at the desired concentration in PBS.

Human tissue culture cALLa-positive NALM-16 leukemia cells were washed and suspended in PBS. One fraction was not treated with antibody (−MoAb). The other fraction was treated with two anti-CD10 and one anti-CD9 monoclonal antibodies (+MoAb) for 30 minutes at 4° C., washed in PBS and adjusted to $3.5 \times 10^6$ cells/ml on PBS. To two tubes, one containing the antibody treated cells (+MoAb), the other containing untreated cells (−MoAb) were added SAM coated magnetic particles at a particle to starting cell ratio of 45. The tubes were rotated at 4° C. for 30 minutes. The particles were separated with a magnetic separator. The supernatant was collected and centrifuged to collect the remaining cells. The pellet was resuspended in 100 ul of trypan blue and total cell count was made. The results were presented in Table IV.

TABLE IV

| Particle/cell Ratio | Cells +/− MoAb | Cells Received | % Depletion |
| --- | --- | --- | --- |
| 0 | + | $7.62 \times 10^5$ | 0 (Control) |
| 45 | + | $2.89 \times 10^4$ | 96.2 |
| 45 | − | $7.33 \times 10^5$ | 4.6 |

EXAMPLE 39

A mixture containing 576 ml of deionized water, 9 ml of styrene, and 288 ml of 3.0% w/v magnetic metal oxide prepared as described in Example 1 was placed in a sealed bottle. The bottle was evacuated and rotated at about 60 rpm in a 65±4° C. oven for one hour. To the mixture were added 18 g of potassium persulfate and 712 ml of 5% w/v, 4.0 micron fluorescent Nile Red polystyrene particles. The bottle was resealed, evacuated and rotated for one hour, and added 45 ml of 2.0% sodium dodecylsulfate. After five more hours, 9 ml of styrene and 9 g of potassium persulfate were added to the mixture. The mixture was rotated for another fifteen hours, filtered through two layers of cheese cloth, separated magnetically, and washed several times with deionized water until the supernatant was clear. The resulting fluorescent magnetic particles were resuspended to 1580 ml with deionized water to give 3.0% w/v suspension with about 11.0% magnetic metal oxide content and 4.4 micron average size.

EXAMPLE 40

The fluorescent Nile Red magnetic particles, 1.580 l of 3.0% w/v, prepared as described in Example 39, were carboxylated by adding 1.23 g of sodium dodecylsulfate, 17.50 g of potassium persulfate, and solution containing 1.2 ml of undecylenic acid and 0.024 ml of divinyl benzene in 4.8 ml of methanol. The mixture was placed in a sealed bottle, evacuated and rotated at about 60 rpm in a 55°–65° oven for five hours. The resulting fluorescent Nile Red carboxyl magnetic particles were separated magnetically and washed several times with deionized water until the supernatant was clear. The fluorescent Nile Red carboxyl magnetic particles were resuspended to 850 ml with deionized water to give a 5.0% w/v suspension with about 11.0% magnetic metal oxide content and 4.4 micron average size.

EXAMPLE 41

A mixture containing 12.4 ml of 11.28% w/v, 2.24 micron polystyrene particles, 65 ml of 2.78% w/v metal oxide prepared as described in Example 5, 75 ml of deionized water and a solution containing 0.18 g of benzoyl peroxide, 7 mg of Nile Red, and 0.75 ml of divinyl benzene in 6.75 ml of styrene was placed in a sealed bottle. The bottle was evacuated and rotated at about 60 rpm in a 60°–70° oven for about fifteen hours. The mixture was filtered through two layers of cheese cloth, separated magnetically, and washed several times with deionized water until the supernatant was clear. The resulting fluorescent crosslinked magnetic particles were resuspended to 170 ml with deionized water to give 5.47% w/v suspension with about 16.5% w/v metal oxide content and 4.0 micron average size.

EXAMPLE 42

The coupling of Goat anti HBsAg to fluorescent and nonfluorescent carboxyl magnetic particles (having about the same as metal oxide content) was similar to Example 30.

To the wells of black 96-well microtiter plate (Pandex™) were added 20 μl of 0.125% w/v, 4.0 micron. Goat anti HBsAg coated thorough mixed fluorescent and nonfluorescent carboxyl magnetic particles (at the ratio 1:1). To the wells containing the magnetic particles was added 100 μl of neat plasma containing various amounts of HBsAg or HBsAg-negative plasma. After thirty minutes of incubation at 37° C., the particles were separated on a magnetic separator and washed twice with 100 μl of wash buffer. To each well containing particles was added 20 μl of mouse anti-HBsAg conjugated to B-galactosidase in dilution buffer. After fifteen minutes incubation at 37° C., the particles were separate and washed six times as described above. To each well containing particles was added 50 μl of a solution containing 4-methylumbelliferyl-B-D-galactopyranoside (MUG, Sgma). The plate was incubated at 37° C. and fluorescence untensity was measured by using a Fluorescence Concentration Analyzer (FCA, Pandex™) equipped with 525 nm excitation and 580 nm emission filters (Channel C, reference Channel) at eight minutes interval and 25×gain setting. The fluorescence intensity in Channel C was recorded in arbitrary fluorescence (AFU) and presented in Table I. The results showed that the fluorescent magnetic particles can detect the empty wells and also indicate the wells with less than average fluorescent intensity; due to the pipetting error on particles loss during the assay.

TABLE I

|  | Channel C (Reference Channel) | |
| --- | --- | --- |
| Nos. of Well | Δ AFU Range | Δ AFU Range |
| 12 Empty | 4832–4900 | 4867 |
| 17 | 29826–33200 | 31480 |
| 1 | — | 19458* |
| 1 | — | 27952 |

*AFU 19458 for one well compare to average AFU 31480 for 17 wells indicative of either loss of particles from particular well or less number of particles delivered at the start of the assay.

EXAMPLE 43

Same procedures as described in Example 42 were followed except fluorescent and nonfluorescent carboxylated magnetic particles coated with Goat anti HBsAg, used simultaneously in the assay to compare the assay performance. The fluorescent intensity was measured by using Channel D (assay channel 365 nm excitation and 450 nm emission filters) and presented in Table II. The results showed that both fluorescent and nonfluorescent particles performed equally in the assay.

TABLE II

|  | AFU | |
| --- | --- | --- |
| HBsAg Conc. | Fluorescent Particles | Nonfluorescent Particles |
| High | 27238 | 30059 |
| Medium | 5820 | 5976 |
| Low | 1688 | 1816 |
| Negative | 326 | 403 |

What is claimed is:

1. A process to determine the presence or concentration of an analyte in a fluid specimen comprising:
    (a) contacting a solution of monodispersed fluorescent magnetic particles having an average diameter from about 1 micron to about 100 microns, a uniform size distribution and magnetic content, comprising an inner fluorescent core polymer particle able to adsorb a monomer, and a coating on said inner fluorescent core polymer particle wherein said coating evenly covers said inner fluorescent core polymer particle, said coating comprising magnetic metal oxide particles of about 1 micron or less in diameter and selected from the group consisting of supermagnetic, paramagnetic and ferromagnetic metal oxide particles and a polymer, wherein said polymer is prepared from monomers which are adsorbable by the inner fluorescent core particle, said fluorescent magnetic particles having a ligand which specifically binds said analyte attached to said fluorescent magnetic particles, with said fluid specimen to form a suspension;
    (b) incubating said suspension until sufficient analyte has reacted with said ligand which specifically binds said analyte;
    (c) separating said magnetic particles from said suspension;
    (d) adding a second labeled ligand which specifically binds said analyte to said separated magnetic particles;
    (e) incubating said suspension until sufficient analyte has reacted with said second labeled ligand which specifically binds said analyte;
    (f) separating said magnetic particles from said suspension;
    (g) detecting or measuring duplex formation on said magnetic particles by means of said label; and
    (h) relating the amount of labeled ligand measured with the amount of analyte measured for a control sample also, said control sample having been evaluated by the same process as the fluid specimen, wherein said fluorescent magnetic particles are used to monitor the number of particles present during said process, wherein the number of said particles is monitored by measuring the fluorescence intensity of fluorescent particles prior to contacting said particles with said fluid specimen and by measuring the fluorescent intensity of fluorescent particles after measuring the amount of labeled ligand associated with said fluorescent magnetic particles.

2. The process of claim 1 wherein the fluorescent magnetic particle contains a fluorescent material selected from the group consisting of Nile red, Coumarin 6, Coumarin 4, Rhodamine B, Nile blue, oxazine 725, oxazine 750, or a mixture of one or more of these fluorescent materials.

3. A process to determine the presence or concentration of an analyte in a fluid specimen comprising:
    (a) contacting a solution of monodispersed fluorescent magnetic particles having an average diameter from about 1 micron to about 100 microns, a uniform size distribution and magnetic content, comprising an inner core polymer particle able to adsorb a monomer, and a coating on the inner core polymer particle wherein the coating evenly covers the inner core polymer particles, said coating comprising a fluorescent dye or combination of fluorescent dyes, magnetic metal oxide particles of about 1 micron or less in diameter and selected from the group consisting of paramagnetic, supermagnetic and ferromagnetic metal oxides and a polymer, said polymer being prepared from monomers which are adsorbable by the inner core polymer particle said fluorescent magnetic particles having a ligand which specifically binds said analyte attached to said fluorescent magnetic particles, with a fluid specimen to form a suspension;
    (b) incubating said suspension until sufficient analyte has reacted with said ligand which specifically binds said analyte;
    (c) separating said magnetic particles from said suspension;
    (d) adding a second labeled ligand which specifically binds said analyte to said separated magnetic particles;
    (e) incubating said suspension until sufficient analyte has reacted with said second labeled ligand which specifically binds said analyte;
    (f) separating said magnetic particles from said suspension;
    (g) detecting or measuring duplex formation on said magnetic particles by means of said label; and (h) relating the amount of labeled ligand measured with the amount of analyte measured for a control sample, said control sample also having been evaluated by the same process as the fluid specimen, wherein said fluorescent magnetic particles are used to monitor the number of particles present during said process, wherein the number of said particles is monitored by measuring the fluorescence intensity of fluorescent particles prior to contacting said particles with said fluid specimen and by measuring the fluorescent intensity of fluorescent particles after measuring the amount of labeled ligand associated with said fluorescent magnetic particles.

4. The process of claim 3 wherein the fluorescent dye or fluorescent dye combination is selected from the group consisting of: Nile red, Coumarin 6, Coumarin 4, Rhodamine B, Nile blue, oxazine 725, and oxazine 750.

* * * * *